United States Patent [19]

Goedemans et al.

[11] Patent Number: 5,395,946
[45] Date of Patent: Mar. 7, 1995

[54] BIFUNCTIONAL CHELATING AGENTS

[76] Inventors: Wilhelmus T. Goedemans, Oude Bergerweg 31, 1862 KJ Bergen; Karel J. Panek, Oudburgerlaan 43, 1852 KN Heiloo, both of Netherlands

[21] Appl. No.: 566,343
[22] PCT Filed: Feb. 8, 1989
[86] PCT No.: PCT/US89/00500
  § 371 Date: Oct. 24, 1990
  § 102(e) Date: Oct. 24, 1990

[30] Foreign Application Priority Data

Feb. 9, 1988 [NL] Netherlands ............... 8800302
Jul. 8, 1988 [NL] Netherlands ............... 8801728
Sep. 30, 1988 [NL] Netherlands ............... 8802408

[51] Int. Cl.⁶ ............ C07D 333/36; C07D 335/02
[52] U.S. Cl. ......................... 549/28; 549/68
[58] Field of Search ..................... 549/68, 28

[56] References Cited

U.S. PATENT DOCUMENTS

| | | | |
|---|---|---|---|
| 3,223,585 | 12/1965 | Addor | 549/28 |
| 3,318,910 | 5/1967 | Addor | 549/6 |
| 3,348,940 | 10/1967 | Addor | 549/68 |
| 4,277,460 | 7/1981 | Kojima et al. | 424/1 |
| 4,652,519 | 3/1987 | Warshawsky et al. | 435/7 |
| 4,659,839 | 4/1987 | Nicolotti et al. | 548/546 |
| 5,183,904 | 2/1993 | Carroll et al. | 549/68 |

OTHER PUBLICATIONS

R. Jue et al., *Biochemistry*, 17 (25), pp. 5399–5406, (1978).

Y. Tamaru et al., *Tetrahedron Letters*, 25 (33) pp. 3583–3586, (1984).

*Primary Examiner*—Richard L. Raymond
*Attorney, Agent, or Firm*—David A. Hey

[57] ABSTRACT

The invention related to a method of preparing a protein or a proteinaceous material labelled with a metalradionuclide and intended for diagnostic or therapeutic application, by reacting a protein or a proteinaceous material with an agent for coupling the radionuclide to the protein or the proteinaceous material, a protein conjugate being formed, and by then complexing the radionuclide with the conjugate thus formed to a radionuclide complex. A coupling agent is used which consists at least substantially of
 a thio compound of the general formula $$Y-R-S-X$$

wherein
 X is a hydrogen atom or a suitable protective group,
 R is a branched or non-branched, optionally substituted hydrocarbon radical having 1–10 carbon atoms, which may be interrupted by one or more hereto atoms, and
 Y is at least one terminal reactive group capable of reacting with a functional group from the protein or the proteinaceous material; or
 a cyclic condensation product of the thio compound of formula I having 5–7 ring atoms, wherein X and Y together constitute a reactive group capable of reacting with a functional group from the protein or the proteinaceous material;
or a water-soluble salt of this condensation product.

3 Claims, 1 Drawing Sheet

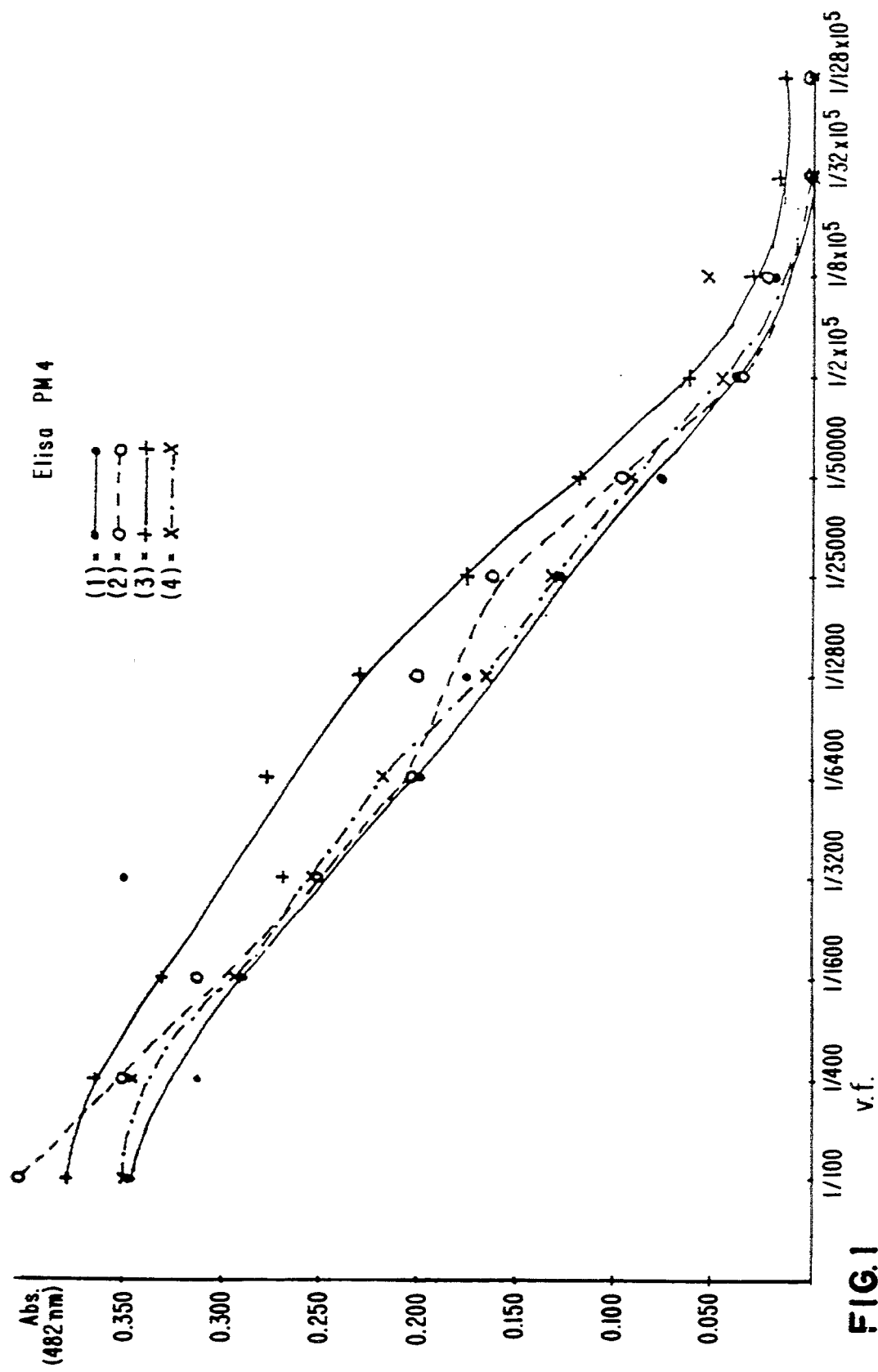

BIFUNCTIONAL CHELATING AGENTS

The invention relates to a method of preparing a metal-radionuclide-labelled protein or proteinaceous material which is destined for diagnostic or therapeutic applications. It also relates to novel compounds useful in this method.

Radionuclide-labelled compounds may be used for diagnostic examinations, for example, into deviations in shape and function of internal organs and into the presence and location of pathological processes in the body. For this purpose a composition in which the radioactive compound is present is administered to the patient, for example, in the form of an injectable liquid. By means of suitable detection apparatuses, for example, a gamma camera, images of the organ or the pathological process in which the radioactive compound has been incorporated can be obtained by recording the emitted radiation, that is, by scanning.

Radioactive labelled biological macromolecules, in particular proteins and proteinaceous materials, for example, blood-cells, immunoglobulins, glycopeptides, monoclonal antibodies, for example, antimyosin and monoclonals against tumor antigens, and other proteins suitable for localization purposes, such as single- or two-chain urokinase, tissue plasminogen activator, plasmin and other plasmin derivatives, e.g., miniplasmin, present interesting perspectives for diagnostic applications. Certain proteins have a very large target organ specificity and, after having been administered into the patient's body, can react very selectively with biological macromolecules present therein; a good example of this is the selective reaction of antibodies or antibody fragments with antigens present in the body.

Various metal-radionuclides, provided they are bonded to tumor-selective biological macromolecules, such as the glycopeptide bleomycin, can successfully be used for the control of tumors and thus form a powerful tool in radiotherapy. The macromolecules used thus serve as vehicles to transport the desired radiation dose, i.e., the metal-radionuclide, to the tumor to be exposed to the radiation.

The direct labelling of a protein or a proteinaceous material with a metal-radionuclide has two disadvantages. First, the biologically active site of the protein necessary for a good target organ specificity or selectivity, may easily be blocked by this reaction so that the normal behavior of the biological macromolecule is disturbed. In addition, the affinity between metal-radionuclide and macromolecule often is insufficient, as a result of which the formed bond is not sufficiently stable to remain intact under physiological conditions. The administered material then is no longer useful, neither as a diagnostic—the behavior of the protein in the body can no longer be traced—nor as a therapeutic—the radiation dose is no longer transported to the desired site but causes an undesired radiation burden elsewhere.

In order to mitigate these disadvantages, it is suggested in European patent application 237150 to first treat proteinaceous substances which contain disulfide bonds with a disulfide reducing agent, for example, dithiothreitol, and to then react the reduced proteinaceous substance which now contains free metcanto groups specifically with a radionuclide species, for example, with Tc-99m-tartrate or -glucoheptonate. The disadvantage of this method is the reductive treatment of the protein, in which the protein is "unfolded" by breaking the disulfide bonds to the desired mercapto groups. Damage to the protein molecules may then easily occur.

In the past few years a great number of publications have appeared in which biological macromolecules, usually proteins or proteinaceous substances, have been described which are provided with chelating groups for a bond with the desired metal-radionuclide. Recent patent publications in this field are the U.S. Pat. Nos. 4,479,930, 4,511,550, 4,652,440 and 4,678,667, the European patent applications (EP) Nos. 83129, 173629 and 188256, the Netherlands patent application (NL) 8204108, and the PCT applications WO 85/03231 and WO 86/03010.

Of course, by this modification the biological behavior of the original macromolecule must be maintained as well as possible. This means that the chelator or the coupling agent with which the metal-radionuclide is bonded to the protein, may not be too bulky, certainly not when used for comparatively small protein molecules. Furthermore, the often extremely sensitive protein or proteinaceous material during the labelling procedure and in particular during the coupling with chelator or coupling agent must be exposed as little as possible to damaging conditions which can adversely influence the properties of the macromolecule. Extended incubations, treatments at elevated temperature, exposure to organic solvents or conditions of pH differing markedly from the physiological pH, and reactions in the presence of oxidizing or reducing agents, all such treatments should be avoided as much as possible. As stated above, the selected coupling agent must ensure a rigid bond between the protein or proteinaceous material on the one hand and the metal-radionuclide on the other. If the bond does not remain intact under physiological conditions, i.e., the radionuclide becomes disassociated in the bloodstream and can be transported by other particles in the blood to undesired sites in the body, the radioactive material can constitute an undesired radiation burden for the tissue at that site, and even if present in therapeutically effective quantities, seriously damage the tissue there. Furthermore, in connection with the often poor storage stability of the labelled macromolecule or the short half-life of the metal-radionuclide used, it is frequently impossible to place the ready-for-use labelled protein or proteinaceous material at the user's disposal. In such cases, the user will perform the labelling reaction with the radionuclide in the clinic or the clinical labortory, for which purpose the various reaction components are then offered to him in a so-called "kit". It will be obvious that the operations to be performed must be as simple as possible, without laborious separation or purification, in order to enable the user to prepare the radioactive labelled protein or proteinaceous material with the means available from the supplied kit. The labelling efficiency or labelling yield also plays an important role. Apart from loss of expensive material, non-converted starting material must be removed from the resulting product in the case of incomplete labelling, as a result of which an elaborate purification of radioactive product under aseptic conditions must usually be carried out by the user.

The chelators or coupling agents described in the patent publications mentioned above leave much to be desired with regard to one or more of the above-mentioned requirements. For example, a comparatively bulk chelator is used in U.S. Pat. Nos. 4,479,930, 4,511,550, 4,678,667 and EP 188256. In order to couple the said chelator to the protein, conditions which are damaging for the protein are used during the coupling reaction in the methods described in U.S. Pat. No. 4,652,440, EP 173629, WO 85/03231 and WO 86/03010. The bond between protein and metal-radionuclide is not sufficiently rigid in the proteins labelled according to U.S. Pat. No. 4,479,930 and WO 85/03231. In many cases the labelling method is laborious and purification of the labelled protein is afterwards necessary, as in U.S. Pat. No. 4,65,2440, EP 83129, EP 188256, NL 8204108, WO 86/03010. Sometimes the labelling is also so incomplete that as a result of this an extra purification step is necessary, as in U.S. Pat. Nos. 4,479,930, 4,652,440, WO 85/03231 and WO 86/03010.

It is the object of the present invention to provide a method of preparing metal-radionuclide-labelled protein or proteinaceous material which is destined for diagnostic or therapeutic applications, by reacting a protein or a proteinaceous material with an agent for coupling the radionuclide to the protein or proteinaceous material, a protein conjugate being formed, and then complexing the radionuclide with the conjugate thus formed to a radionuclide complex, the disadvantages mentioned above not occurring or occurring to a considerably lesser extent than in the methods of preparation described in the above-mentioned patent publications.

This object can be achieved by using in the preparation a coupling agent which consists at least substantially of a thio compound of the general formula

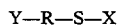  (I)

wherein
X is a hydrogen atom or a suitable protective group,
R is a branched or non-branched, optionally substituted hydrocarbon radical having 1-10 carbon atoms preferably 1-4 carbon atoms and more preferably alkyl, which may be interrupted by one or more hereto atoms, and
Y is at least one terminal reactive group capable of reacting with a functional group from the protein or the proteinaceous material; or
a cyclic condensation product of the thio compound of formula I having 5-7 ring atoms, wherein X and Y together constitute a reactive group capable of reacting with a functional group from the protein or the proteinaceous material;
or a water-soluble salt of this condensation product.

Examples of suitable protective groups X for the mercapto group are: acetyl, trifluoroacetyl, hydroxyacetyl, carboxyacetyl, acetamidomethyl, benzoyl, benzyl, benzoylaminomethyl and other groups suitable for protecting sulfur atoms from oxidation.

Examples of metal-radionuclides suitable for use in the methods according to the invention in radio-labelling amounts, i.e., in diagnostic or therapeutic amounts, are Tc-99m, Re-186, Re-188, Cu-67, Pb-203, Pb-212, Ga-67, Ga-68, Bi-212, As-72, As-77, In-111, In-113, Ru-97, Y-90, Ag-111, Pd-109, Sm153, Yb-175, Lu-177, and Gd-159. Of these radionuclides Tc-99m, Pb-203, Ga-67, Ga-68, As-72, In-111, In-113 and Ru-97 may be used for diagnostic purposes. The other radionuclides are useful in particular in therapeutically active compositions.

In the complex formation reaction the desired radionuclide is presented to the protein conjugate in the form of a salt or preferably in the form of a chelate bonded to comparatively weak chelators, for example, a pyrophosphate, a phosphonate or polyphosphonate, an oxinate, a carboxylate, a hydroxycarboxylate, an aminocarboxylate, an enolate or mixtures thereof, also in a neutral medium. In the latter case the desired complex is formed via the principle of ligand exchange, in which the sulfur atom of the thio compound forms a strong chelate bond with the metal-radionuclide.

The derivatisation of the protein or proteinaceous material, i.e., the reaction with the coupling agent, may be carried out under a wide range of conditions. These will vary with the particular coupling agent chosen and the nature of the protein or proteinaceous material desired to be labelled. The pH of the reaction medium is preferred to be between 6.5 and 9, more preferably between 7 and 8.5. The incubation may be carried out at any temperature that does not seriously affect the physical structure of the protein or proteinaceous material. It is preferred that the temperature be around room temperature. The incubation time can range from a few minutes to several hours. A preferred range is 20 minutes to two hours.

The coupling agent and protein or proteinaceous material may form a conjugate that consists of one or more coupling molecules per polypeptide molecule. Larger polypeptides have potentially more reactive sites, and thus more coupling molecules can be conjugated with it. For example, for immunoglobulins a preferred ratio is 5 moles coupling agent to 1 mole protein. For albumin a preferred ratio is 2.5 to 1. The range for larger proteins is generally from about 0.5 to about 20 moles coupling agent per mole protein. However, smaller proteins or proteinaceous materials are preferably contacted with lower ratios of coupling agent to polypeptide in order to prevent aggregation of the peptide chains. For example, for somatostatin the preferred ratio is 0.1 to 1. The range for smaller proteins or protein fragments is from about 0.01 to about 2 moles coupling agent per mole of protein or proteinaceous material.

For the method according to the invention, a preferred coupling agent is
a thio compound of the general formula

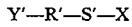  (II)

wherein
X has the meaning given above;
R' is a branched or non-branched, optionally substituted hydrocarbon radical having 1-10 carbon atoms, which may be interrupted by one or more hetero atoms selected from O, N and S and/or one or more NH groups; and
Y' is an isocyanato group; a formyl group; an orthohalonitrophenyl group; a diazonium group; an isothiocyanato group; an epoxy group; a trichlorostriazinyl group, an ethylene imino group; a chlorosulfonyl group; an alkoxycarbimidoyl group; a substituted or non-substituted alkylcarbonyloxycarbonyl group; a substituted or non-substituted alkylcarbonylimidazolyl group; or a sulfonated or non-sulfonated N-hydroxy-succinimide ester group (succinimidooxycarbonyl group); or
a cyclic condensation product of the thio compound of formula II having 5-7 ring atoms, wherein X and Y together constitute one of the following groups;

a carbonyl group, a carbimidoyl group, an N-alkylcarbimidoyl group, an N-hydroxycarbimidoyl group or an N-alkoxycarbimidoyl group;
or a water-soluble salt of the said condensation product.

When R' is a substituted hydrocarbon radical, these substitutents may be selected from groups which may be capable of chelating with the metal-radionuclide, thus forming a polydentate ligand for the metal-radionuclide. Examples of such groups are protected or non-protected mercapto groups, carboxyl groups, hydroxyl groups, amino groups, and the like.

When in the above meanings an alkyl group is mentioned, it is preferably a group of one to four carbon atoms. Water-soluble salts include salts with various acids, for example, hydrochloric acid, sulfuric acid, phosphoric acid, perchloric acid and organic acids, for example, citric acid, tartaric acid, and the like.

Suitable cyclic coupling agents have the general formula $$X-S-R''-C\begin{matrix}\nearrow NH \\ \searrow OR'''\end{matrix} \quad (III)$$

wherein
X has the meaning given above;
R'' is a branched or non-branched alkyl group unsubstituted or substituted with one or more XS groups and having 1–10 carbon atoms; and
R''' is an alkyl group having 1–4 carbon atoms;
or a water-soluble salt.

A preferred example of a compound of Formula III is:

$$H_3C\underset{NH}{\overset{\|}{\diagdown}}\diagup\diagdown\diagup S-X$$

Pre-eminently suitable has been found to be novel compounds of the general formula $$\begin{matrix} R_4 & R_4' \\ R_3' & R_5 \\ R_3 & R_5' \\ R_2' & \\ R_2 & S & NR_6 \end{matrix} \quad (IV)$$

wherein
$R_2$, $R_2'$, $R_3$, $R_3'$, $R_4$, $R_4'$, $R_5$ and $R_5'$ are equal or independently hydrogen atoms, alkyl groups, XS-alkyl groups, alkylthioalkyl groups, alkylcarbonylthioalkyl groups, aminoalkyl groups, N-alkylaminoalkyl groups, N-alkylcarbonylaminoalkyl groups or N,N-dialkylaminoalkyl groups, wherein X has the meaning given hereinbefore and the alkyl groups have 1–4 carbon atoms;
n is 0 or 1; and
$R_6$ is a hydrogen atom or an alkyl group having 1–6 carbon atoms;
or a water-soluble salt of this compound.

Due to the stability, easy handleability, selectivity with respect to free $NH_2$ groups of the protein and especially simple and easy coupling reaction without the formation of undesired byproducts, is to be preferred a coupling agent of the general formula $$(H_3C)_{\overline{p}}\diagup\diagdown(CH_2Z)_q \quad (V)$$
$$\diagdown S \diagup NR_6$$

wherein
$R_6$ and n have the above meanings,
p is 0 or 1,
q is 0 or 1, and
Z is a hydrogen atom, a $C_1$–$C_4$ alkyl group, a mercapto group, a $C_1$–$C_4$ alkylthio group or a $C_2$–$C_5$ alkanoylthio group;
or a water-soluble salt of this compound.

The protein conjugate formed by using this coupling agent is particularly suitable for complexing with metal-radionuclides, in particular with Tc-99m. In addition to the unsubstituted 2-iminothiolane and 2-iminothiacyclohexane, examples of excellently suitable 2-iminothio-compounds are: alkyl-substituted 2-iminothiolanes like 2-N-methyliminothiolane, 4-methyl-2-iminothiolane, 2-N-tert-butyliminothiolane and 4,4-dimethyl-2-iminothiolane, and iminothiolanes with thio or amino functions like 4-mercaptomethyl-2-iminothiolane, 4-acetylthiomethyl-2-iminothiolane, 4-ethylthiomethyl-2-iminothiolane and 4-methylaminomethyl-2-iminothiolane. As will be clear from the Examples, when using 4-acetylthiomethyl-2-iminothiolane as a coupling agent a protein can be labelled with technetium-99m in a yield of even 100%.

Jue and collaborators described the use of 2-iminothiolane for the modification of proteins in 1978: Biochemistry Vol. 17, No. 25, 1978, 5399–5406. Perham and Thomas describe in J. Mol. Biol. (1971) 62, 415–418 a subsequent reaction of a protein modified in such a manner with a mercury compound to allow clarification of the structure of the protein. The use of proteins modified in this manner for the preparation of proteins labelled with a metal-radionuclide and the favorable biological property of the labelled proteins thus obtained were not known.

Substituted 2-iminothiolanes and 2-iminothiacyclohexanes which may be used as coupling agents in the preparation of labelled proteins or proteinaceous materials are new. The invention, therefore, also relates to compounds of the above general formula IV, wherein the symbols have the means given above, with the proviso that not all the substituents $R_2$, $R_2'$, $R_3$, $R_3'$, $R_4$, $R_4'$, $R_5$, $R_5'$ and $R_6$ together represent hydrogen atoms.

More in particular these new compounds may be characterized by the above general formula V, wherein the symbols also have the meanings given before, with the proviso that $R_6$ is a $C_1$–$C_6$ alkyl group if p and q are both 0.

In addition, the invention relates to protein conjugates formed by reacting proteins or proteinaceous materials with the above new compounds as coupling agents.

The invention also relates to a protein or a proteinaceous material labelled with a metal-radionuclide obtained by using the method as described above, and to a radiopharmaceutical composition which, in addition to a pharmaceutically acceptable liquid carrier material, contains a protein or a proteinaceous material labelled with a metal-radionuclide. The resulting solution of the labelled protein or proteinaceous material may be used directly as a radiopharmaceutical composition. If necessary, the solution may be brought into a form more suitable for intravenous or subcutaneous administration, for example, by a purification or by the addition of a pharmaceutically acceptable liquid carrier material, preferably a physiological saline solution. Of course, it should be ensured that during the said treatment the protein is not damaged. It will be evident that the solution should be sterile for intravenous or subcutaneous administration.

For performing a radiodiagnostic examination, the composition, as described above, if desired after dilution with a pharmaceutically acceptable liquid, preferably a physiological saline solution, may be administered to a warm-blooded living being in a quantity from 100/uCi to 30 mCi, preferably from 0.5 to 10 mCi, per 70 kg of body weight, after which the radioactive radiation emitted by the being is recorded.

If the composition is to be used for a radiotherapeutic treatment, a suitable metal-radionuclide should be selected for the labelling reaction, as indicated above. Upon use, the composition, if desired after dilution with a pharmaceutically acceptable liquid, is administered to a warm-blooded living being in a quantity effective for combating or controlling tumors.

Since the radiopharmaceutical composition according to the invention can be prepared so easily and simply, the preparation can be performed particularly readily by the user himself. The invention, therefore, also relates to a so-called "kit" as described above, containing (1) in an optionally dry condition a preparation of a protein conjugate which is formed by reaction of a protein or proteinaceous material with a coupling agent consisting at least substantially of a thio compound or a cyclic condensation product thereof, as defined above, (2) a solution of a salt or chelate of a metal-radionuclide, and (3), if desired, instructions for use with a prescription for reacting (1) with (2). As stated above, for this complexing reaction the desired radionuclide is preferably presented to the protein conjugate in the form of a chelate bonded to a comparatively weak chelator, for example, a pyrophosphate, a phosphonate or polyphosphonate, an oxinate, a carboxylate, a hydroxycarboxylate, an aminocarboxylate, an enolate or mixtures thereof, in which the reaction can take place in a neutral medium. Examples of suitable chelators for the radionuclide are 8-hydroxyquinoline or derivatives thereof; dicarboxylic acids, polycarboxylic acids or hydroxycarboxylic acids, for example, oxalic acid, malonic acid, succinic acid, maleic acid, ortho-phthalic acid, malic acid, lactic acid, tartaric acid, citric acid, ascorbic acid, salicylic acid or derivatives of these acids; pyrophosphates; phosphonates or polyphosphonates, for example, methylene diphosphonate, hydroxyethylene diphosphonate or hydroxymethylene diphosphonate; or enolates, for example with $\beta$-diketone, such as acetyl acetone, furoyl acetone, thenoyl acetone, benzoyl acetone, dibenzoyl methane, tropolone or derivatives of these diketones. 8-Hydroxyquinoline, citric acid, tartaric acid, ascorbic acid, glucoheptonic acid or a derivative hereof, or acetyl acetone are to be considered particularly suitable because it has been proven that a chelate of a radionuclide, e.g., indium-111 or lead-203, with one of these chelators in a suitable medium, preferably a buffered aqueous solution, easily reacts at a physiological pH with a protein conjugate as defined above, the desired radionuclide complex being formed by ligand exchange in a high yield and purity. A buffered aqueous indium-111-tropolonate solution suitable for this purpose, which may be used for the desired complex formation, has been described in European patent application no. 131327 incorporated herein by reference. The supplied kit may also contain the constituent mentioned sub (1) with, optionally, instructions for use, whereas the solution of the metal-radionuclide defined sub (2), having a limited shelf life, can be supplied separately to the user.

In another equally extremely favorable embodiment, the kit according to the invention is equipped so as to contain the following ingredients: (1) in an optionally dry condition a preparation of a protein conjugate formed by reaction of a protein or a proteinaceous material with a coupling agent, consisting of a thio compound or a cyclic condensation product thereof, as defined above; (2) a chelator as described above and a reducing agent; and (3) if desired, instructions for use With a prescription for reacting ingredients ( 1 ) and (2) with technetium-99m in the form of a pertechnetate solution. The composition should comprise a reducing agent to reduce the pertechnetate, for example, a dithionite or stannous ions. Such a kit is intended for the preparation of a Tc-99m-labelled pharmaceutical composition. The pertechnetate solution can simply be obtained by the user from a molybdenum-technetium generator available for this purpose. A similar kit may be used for the preparation of a Re-186 or Re-188 labelled pharmaceutical composition in which the perrhenate solution should also be reduced with a suitable reducing agent, for example, a dithionite or stannous ions. If desired, the above ingredients defined sub (1) and (2) may be combined, provided they are compatible, i.e., the protein conjugate is not attacked by any of the constituents mentioned sub (2).

Such a monocomponent kit, in which the combined ingredients are preferably lyophilized, is excellently suitable for being reacted by the user with the radionuclide solution in a simple manner.

In again another likewise excellently suitable embodiment, the kit, according to the invention, is equipped so that it contains (1) in an optionally dry condition a coupling agent, consisting at least substantially of a thio compound as defined above, as well as a chelator as described above and a reducing agent, and (2) if desired, instructions for use with a prescription for reacting the ingredients mentioned sub (1) which are preferably accommodated in one vial, with a protein which is separately supplied to the user, and with technetium-99m in the form of a pertechnetate solution or with rhenium-186 or rhenium-188 in the form of a perrhenate solution. By means of this so-called "multipurpose" kit, the user can hence label any desired protein available with radioactive technetium or rhenium, in which the protein conjugate required therefor is hence formed intermediately.

In an embodiment related to this last kit, the kit, according to the invention, contains (1) a coupling agent as defined above, (2) a solution of a salt or chelate of a metal-radionuclide, and (3) if desired, instructions for use with a prescription for reacting (1) with (2).

A metallic reducing agent, for example Sn(II), Fe(II), Cu(I), Ti(III) or Sb(III), is preferably used as a reducing agent for the above-mentioned kits; Sn(II) is preferred. It is a generally accepted fact that the quantity of reducing agent has no influence on the results; see, for example, the note in question in the PCT Patent Application WO 87/04164, p. 7. It has now been found surprisingly that not only an extremely small quantity of metallic reducing agent suffices, namely from 0.1 to 10/ug of metal per mg of protein conjugate or protein, preferably 1–4/ug per rag, but that the labelling efficiency as well as the stability of the labelled product are considerably improved when such a small quantity of reducing agent is used. This will be described in greater detail in the specific examples.

The constituent (of the kits mentioned above) sub (1) may be supplied as a solution, for example, in the form of a physiological saline solution, or in a buffer solution, but is preferably present in a dry condition, for example, in a lyophilized condition. When used as a component for an injection it should be sterile. So if the constituent is present in a dry condition, a sterile physiological saline solution would be used as a solvent. If desired, the above constituent may be stabilized in a conventional manner using suitable stabilizers like ascorbic acid, gentisic acid or salts of these acids, or be provided with other auxiliary agents, for example, fillers like glucose, lactose, mannitol, and the like.

The invention will now be described in greater detail with reference to the ensuing specific examples.

EXAMPLE I

Modification of albumin with 2-iminothiolane

Starting material is 0.5 ml of human albumin in a concentration of 5 mg/ml in 0.06M triethanolamine-HCl, pH 8.0. To this solution 25/ul of a 0.5M 2-iminothiolane solution in 1M triethanolamine-HCl, pH 8.0, are added. The incubation is carried out at room temperature for one hour. A successful coupling of a 2-iminothiolane molecule to a lysine $NH_2$ group on the protein provides one extra —SH group. The course of the reaction is measured by determining the number of —SH groups prior to and after reaction with 2-iminothiolane. The —SH determination is carried out according to Grassetti, et al., "The Determination of Thiols and of Total Glutathione in Human Blood Using 6,6'-Dithiodinicotinic Acid (CPDS)" in *Biochemical Medicin* 12; pp. 149–153 (1975). The principle of the determination is as follows: CPDS reacts with thiols (SH-groups) while forming 6-mercaptonicotinic acid (6-MNA) and a disulfide. At 344 nm, 6-MNA is determined spectrophotometrically, after which the molar thiol concentration is calculated on the starting substance. The number of —SH groups on the protein prior to 2-iminothiolane modification is 1.57. After modification this is 25.92.

EXAMPLE II

Albumin modification with 2-iminothiolane and labelling with Tc-99m glucoheptonate Starting material is 2.5 ml of human albumin in a concentration of 5 mg/ml in 0.06M triethanolamine-HCl, pH 8.0. To this solution 25/ul of a 0.5M 2-iminothiolane solution in 1M triethanolamine-HCl, pH 8.0, are added. The incubation is carried out at room temperature for 1.5 hours. 1 ml of the reaction is purified by means of gel chromatography (Sephadex G25). Another 1 ml of sample was not purified.

Purified and unpurified modified albumin are then contacted with 0.2 ml of Tc-99m glucoheptonate, corresponding to 4.5 mCi. Analysis of Tc-99m labelling of both samples is carried out after 20 minutes and after incubation at room temperature for 2 hours. The analysis method is gel chromatography over Sephadex G25.

The labelling yield of the purified modified albumin sample after 20 minutes of incubation is 40.8%; after 2 hours of incubation this is 85.6%.

The labelling yield of the unpurified modified albumin sample after 20 minutes of incubation is 88.7%; after two hours of incubation this is 93.2%.

EXAMPLE III

Determination of the stability of the Tc-99m label on 2-iminothiolane-modified albumin in DTPA medium Excess of DTPA (diethylenetriamine pentaacetic acid) is added to the purified Tc-99m-labelled samples of Example II. The ratio DTPA:protein is 5:1.6 on the basis of units by weight. The DTPA-containing Tc-99m-labelled albumin samples are incubated at room temperature for 48 hours. The degree of Tc-99m bonding to albumin is then determined by means of gel chromatography using Sephadex G25. The bonding degree is 97.3% of the originally present Tc-99m label (corrected for radioactive decay). This means that only 2.7% of the label of the albumin has disappeared.

EXAMPLE IV

Ig (immunoglobulin) modification by means of 2-iminothiolane and labelling with Tc-99m glucoheptonate Starting material is 2.5 ml of human Ig in a concentration of 10 mg/ml in 0.06M triethanolamine-HCl, pH 8.0. To this solution 25/ul of a 0.5M 2-iminothiolane solution in 1M triethanolamine-HCl, pH 8.0, are added. The incubation is carried out at room temperature for 1 hour. 2 ml of Tc-99m glucoheptonate (=224 mCi) are then added to 2.5 ml of reaction mixture and incubated for 30 minutes.

The labelling yield is 73.6% measured by analysis via gel chromatography.

EXAMPLE V

Ig immunoglobulin modification with 2-iminothiolane and labelling with Tc-99m tartrate. Comparison with Tc-99m glucoheptonate Starting material is 1 ml of human Ig in a concentration of 10 mg/ml in 0.06M triethanolamine-HCl, pH 8.0. To this solution 5/ul of 0.18M 2-iminothiolane in 1M of triethanolamine-HCl, pH 8.0, are added. After incubation at room temperature for 1 hour, this reaction mixture is divided into 2 portions of 0.5 ml. 1 ml (10 mCi) of Tc-99m glucoheptonate is added to one portion and 1 ml (10 mCi) of Tc-99m tartrate is added to the other portion. After incubation for 45 minutes the mixtures are analyzed by means of gel chromatography (Sephadex G25).

The labelling yield for the Tc-99m glucoheptonate labelling is only 17% as a result of the small amount of 2-iminothiolane presented, but for Tc-99m this is considerably higher, namely 58%. Blank labelling experiments with non-modified Ig provide no labelling of the protein.

EXAMPLE VI

Determination of the stability of the Tc-99m label on 2-iminothiolane modified Ig (immunoglobulin) in serum 5/ul of 0.07M 2-iminothiolane in 1M triethanolamine-HCl, pH 8.0, are added to 0.1 ml of a solution containing 1 mg of Ig in 0.06M triethanolamine-HCl (pH 8.0). The reaction time is 1 hour at room temperature. 0.5 ml of Tc-99m tartrate (=42.7 mCi) are added and the mixture is incubated at room temperature for 1 hour. After analysis the labelling yield is 72.7%. After two hours to two 0.1 ml-samples of this unpurified reaction mixture are added 0.5 ml of human serum (first 0.1 ml-sample), and 0.5 ml of physiological saline solution (second 0.1 ml-sample), respectively. 0.5 ml of human serum are also added to a non-modified, but Tc-99m tartrate-containing Ig sample (blank). After incubation at room temperature for 24 hours the samples are analyzed for Tc-99m bonding to the Ig by means of gel chromatography. The bonding is 91% for the Tc-99m 2-iminothiolane modified Ig. This is equally 91% if incubated in physiological saline solution. The unmodified Ig in serum has a non-specific bonding of 45% (to serum proteins). The conclusion is that incubation in serum has not detached any Tc-99m from the protein.

EXAMPLE VII

Determination of the immunoreactivity of Ig (immunoglobulin) after modification with 2-iminothiolane and labelling with Tc-99m tartrate and Tc-99m glucoheptonate The immunoreactivity is determined by means of affinity chromatography. For this purpose, the Ig fraction of antihuman Ig generated in goats is covalently bonded to cyanogen bromide-activated, cross-linked agarose in the form of small spheres. With these a small column is made in a 2 ml-syringe. This column can bind approximately 0.6 mg of human Ig at neutral pit. The column is validated by elution with native (untreated) Ig and albumin in PBS (phosphate-buffered saline). In the case of Ig the column shows optimum retention (60–80%). In the case of albumin the column shows hardly any retention (5%). The column is stripped by washing with 0.1M glycine in 0.15M NaCl, pH 2.4. The immunoreactivity as a percentage of a Tc-99m-labelled Ig sample is then defined as follows:

retention % Tc-99m Ig/retention % native Ig (the same medium)×100

In the case of the Ig of Example V in a ratio 1: 10 modified with 2-iminothiolane and labelled with Tc-99m tartrate, the immunoreactivity is 99.4% of that of the original Ig. After Tc-99m glucoheptonate labelling the immunoreactivity is 94.9%.

EXAMPLE VIII

Monoclonal antibody modification by means of 2-iminothiolane and labelling with Tc-99m tartrate The monoclonal antibody used has been generated in mice and is directed against human CEA (carcino-embryonic antigen) and can in principle be used, after labelling, for detecting colon tumors. The antibody is termed Parlam 4.5/ul of 0.077M 2-iminothiolane in 1M triethanolamine-HCl, pH 8.0, are added to 0.1 ml of a solution containing 1 mg of Parlam in PBS (phosphate-buffered saline, pH 7.6). The reaction time is 1 hour at room temperature. 0.5 ml of Tc-99m tartrate (=8 mCi) are added and incubation at room temperature is carried out for 1.5 hours. After analysis by means of gel chromatography the labelling yield is 79.5%.

EXAMPLE IX

Determination of the immunoreactivity of monoclonal antibody after modification with 2-iminothiolane and labelling with Tc-99m tartrate The immunoreactivity is determined by means of the so-called Elisa test using CEA (carcino-embryonic antigen) as an antigen. The procedure has been described by Lamsdorp, et al. in *J. Immunol. Methods* 39,293–405 (1980), "Immunoperoxidase procedures to detect monoclonal antibodies against cell surface antigens. Quantitation of binding and staining of individual cells". CEA in PBS (phosphate-buffered saline) with 1% BSA (bovine serum albumin) is added to the wells of a 96-well microtiter plate and preincubated at room temperature. Parlam 4 antibody in PBS with 1% BSA (dilutd 1 to 100, starting from 10/ul/ml) is then added and stepwise further diluted. After incubation the wells are washed three times with PBS (0.05% Tween ® 20) and treated with antimouse Ig (diluted 1 to 400) generated in rabbits and labelled with peroxidase. After incubation and washing three times with PBS (0.05% Tween 20), substrate (o-phenylenediamine 1 mg/ml in 0.1M acetate, pH 5.0) is added and after developing the color reaction, the absorption at 482 nm is determined by using a spectrophotometer.

In the comparison are incorporated: (1) modified Parlam 4 (PM 4) antibody of Example VIII; (2) modified PM 4 antibody labelled with Tc-99m tartrate of Example VIII; (3) Parlam 4 not modified but in the presence of Tc-99m tartrate and (4) Parlam 4 in ascites liquid.

DESCRIPTION OF THE DRAWING

The graph of FIG. 1 indicates that 2-iminothiolane modification and labelling with Tc-99m tartrate have no measurable influence on the immunoreactivity. "Abs" in the graph denotes the measured absorption and "v. f." denotes the dilution factor. The curves and samples are related as follows:

(1) . - - - - - . Parlam 4 (PM 4) 2-iminothiolane modified;
(2) O - - - - - O PM 4 2-iminothiolane modified, Tc-99m tartrate labelled;
(3) +- - - - - + PM 4+Tc-99m tartrate;
(4) X - - . - - X PM 4 ascites liquid.

EXAMPLE X

Albumin modification by means of 2-iminothiolane and labelling with Pb-203 citrate Starting material is 2.5 ml of albumin in a concentration of 5 mg/ml in 0.06M triethanolamine-HCl, pH 8.0. To this solution are added 10/ul of a 0.5M 2-iminothiolane solution in 1M triethanolamine-HCl, pH 8.0. The incubation is carried out at room temperature for 65 minutes. 1 ml of the reaction mixture is purified by means of gel chromatography (Sephadex G25). This provides 1.5 ml of modified albumin in a concentration of 3.3 mg/ml. 1 ml of Pb-203 citrate (=0.5 mCi) is added and incubation is carried out at room temperature for 45 minutes. Analysis by means of gel chromatography indicates that the labelling yield is 75%. Non-modified albumin provides no labelling yield whatsoever under the same labelling conditions.

EXAMPLE XI

Ig (immunoglobulin) modification by means of 2-iminothiolane and labelling with In-111 tropolonate Starting material is 3 ml of Ig solution in a concentration of 10 mg/ml in 0.06M triethanolamine-HCl, pH 8.0. To this solution 25/ul of a 0.5M 2-iminiothiolane solution in 1M triethanolamine-HCl, pH 8.0 are added. The reaction time is 1 hour at room temperature. 0.5 ml of the reaction mixture is purified by gel filtration (Sephadex G25). This provides 1.5 ml of modified Ig comprising approximately 5 mg of modified protein. To this are added 0.3 ml In-111 tropolonate (0.3 mCi). 0.3 ml of In-111 tropolonate are also added to 0.5 ml of unpurified modified Ig. After incubation at room temperature for 30 minutes the labelling yields are determined by gel chromatography. These yields are both 100% for purified and unpurified modified Ig. Under the same labelling conditions non-modified Ig gives a labelling yield of 41%.

EXAMPLE XII

Preparation of a multipurpose kit

200/ug of 2-iminothiolane and 5/ug of Sn(II) in the form of tin tartrate are combined in a vial; both components are lyophilized.

This multipurpose kit may be used for labelling all kinds of proteins. For example, 2 ml of a saline solution containing 200 mg of human Ig are added, the whole is mixed, after which labelling is carried out with 10 mCi (370 MBq) of pertechnetate in 0.5 ml of physiological saline solution. After incubating at room temperature for 10 minutes the labelling yield is determined by elution over Sephadex G25 column; it is 91.9%.

EXAMPLE XIII

Preparation of a monocomponent kit and use of a composition prepared by means of the same Human Ig is modified with 2-iminothiolane as described in Example V, and lyophilized. 1 mg of this modified protein, 5 mg of tartaric acid and 2/ug of Sn(II) in the form of tin chloride are combined in a vial.

This kit is labelled with technetium-99m as follows: 0.5 ml of 0.5 mCi pertechnetate from a molybdenum-technetium generator are added to the vial, after which incubation is carried out for 20 minutes at room temperature; the labelling yield is 99.2%.

The labelled product is used for localizing an infectious process in abscess-carrying mice. For that purpose this product, in this case the radiopharmacon, is administered intravenously to mice, in which 16 hours previously an infection (*Staphylococcus aureus*, 8–12 million units) had been produced in the muscles of the right thigh. Scintigrams are made at 1, 6 and 24 hours after the intravenous injection and are compared with those of corresponding sites of the left, non-infected thigh. The results, i.e., the ratio R:L=infected right thigh:-non-infected left thigh, are recorded below. For comparison, corresponding experiments have been carried out using a radiopharmacon frequently used for this purpose, namely gallium-67 citrate. The results from four test animals have been averaged.

| Radiopharmacon | Radio R : L after | | |
|---|---|---|---|
| | 1 hour | 6 hours | 24 hours |
| Tc99m-Ig | 3.32 | 3.79 | 6.58 |
| Ga 67-citrate | 1.60 | 1.90 | 1.92 |

The differences between the tested radiopharmacons are evident.

EXAMPLE XIV

Comparison of tin content in a kit to be labelled 1 mg of Ig modified with 2-iminothiolane and prepared according to Example V is mixed in a vial with 1.39/ug of Sn(II) in the form of tin tartrate. 5 mCi (185 MBq) of pertechnetate in 0.5 ml of physiological saline solution are added to this vial after which the mixture is incubated at room temperature for 20 minutes. The labelling yield is then determined by elution over a Sephadex G25 column and is 93.8%.

When repeating the above experiment in the presence of 12.5/ug of Sn(II) in the form of tin tartrate a labelling yield of only 74.9% is reached.

EXAMPLE XV

Preparation of a two-component kit and use of a composition prepared by means of the same One vial contains 1 mg of Ig modified with 2iminothiolane, prepared as described in Example V, the other one contains 25 mg of tartaric acid and 20/ug of Sn(II) in the form of tin chloride. Both components are in the lyophilized form.

The labelling of the kit is carried out as follows: 5 ml of physiological saline solution are added to the vial containing tartaric acid+Sn(II). 1 ml of the resulting solution is added to the vial containing modified Ig and the whole is mixed. Pertechnetate is then added, mixed and incubated as in Example XIII.

The pharmacon is tested in mice in comparison with gallium-67 citrate, exactly as described in Example XIII. The results, i.e., the ratio R: L are recorded in the table below. The results of four test animals have been averaged.

| Radiopharmacon | Radio R : L after | | |
|---|---|---|---|
| | 1 hour | 6 hours | 24 hours |
| Tc99m-Ig | 3.04 | 4.71 | 6.55 |
| Ga 67-citrate | 1.60 | 1.90 | 1.92 |

In this test also the differences with the known product are evident.

EXAMPLE XVI

Preparation of 2-imino-4-methylthiolane and albumin modification and labelling a) Air is drawn through 9.28 g of distilled methylallylchloride through a $CaCl_2$-tube for 90 minutes: HBr is then passed through while cooling for 3 hours. The resulting 1-bromo-3-chloro-2-methylpropane, after washing successively with water, $K_2CO_3$-solution and water, is distilled in vacuo and identified by means of the NMR spectrum; yield 15.5 g.

b) NaCN in a quantity of 1.43 g is dissolved in 2.5 ml of water, after which 10 ml of ethanol and 5 g of the compound obtained sub a) are added. The reaction mixture is refluxed at approximately 85° C. for 20 hours and worked up as follows: evaporation of ethanol; addition of methylene chloride and filtering of NaBr; drying, evaporating and distilling in vacuo. The desired product (identification by means of NMR spectrum), namely 3-chloro-2-methylpropylcyanide, is obtained in a yield of 1.75 g.

c) 0.5 g of the compound obtained sub b) is added while stirring to a solution of 0.534 g of potassium thioacetate (KSAc) in 0.7 ml of dry dimethyl sulphoxide (DMSO). After stirring at room temperature for 1 hour the reaction mixture is worked up by addition of water, extraction with diethyl ether, washing of the ether phase with concentrated NaCl-solution, and drying the ether phase. After evaporating the diethyl ether the product is distilled in vacuo. 3-Acetylthio-2-methylpropylcyanide is obtained in a yield of 0.365 g; identification by means of NMR-spectrum and IR-spectrum.

d) The product obtained sub c) is cyclized by stirring 0.77 g in 2.14 of dry methanol and 2.95 ml of 7.6N HCl/methanol for 48 hours. After evaporating methanol/HCl and cooling, diethylether is added. The crystalline 3-imino-4-methylthiolane is filtered off and washed with diethyl ether; melting-point 175°–177° C.

Human albumin is modified with the resulting 2-imino-4-methylthiolane in the same manner as described for 2-iminothiolane in Example I and then labelled with Tc-99m by the addition of 2/ug of Sn(II) and 5 mg of tartaric acid as sodium salt in a physiological saline solution and then of 0.5 ml of Tc-99m pertechnetate, likewise in a physiological saline solution, corresponding to approximately 5 mCi (185 MBq). The labelling yield is 96.9%.

EXAMPLE XVII

2-Iminothiacyclohexane

In a corresponding manner as described in Example XVI the title compound is prepared starting from ω-bromobutylcyanide; melting point 182° C.

Human albumin is modified with 2-iminothiacyclohexane as describd in Example I and then labelled with Tc-99m as described in Example XVI. The labelling yield is 83.4%.

EXAMPLE XVIII

Preparation and use of 2-N-tert-butyliminothiolane a) A solution of 35 g 4-chlorobutyrylchloride in 100 ml of diethylether is added dropwise to a stirred solution of 19 g tert-butylamine and 28 g triethylamine in 400 ml of diethylether. After reflux for one hour the mixture is poured into water, the organic phase is separated and the water layer is extracted with diethylether. The combined organic phase is successively washed with water and saturated NaCl solution, and then dried. After evaporating the solvent, 4-chloro-N-tert-butylbutyric amide is obtained in a yield of 40.8 g. The product can be purified by recrystallization from methanol: m.p. 62.5°–64° C.

b) To a stirred and refluxed solution of 7.1 g of the above amide in 300 ml of toluene, 17.8 g of $P_4S_{10}$ is added portionwise. After reflux for 60 hours and cooling, the mixture is poured on a saturated NaHCO$_3$ solution. The organic layer is separated, washed successive with a saturated NaHCO$_3$ solution (twice) and a saturated NaCl solution, and dried. After evaporating the solvent the title compound, 2-N-tert-butyliminothiolane, is obtained as a yellow liquid: b.p. 115°–117° C./40 mm Hg. The product is identified by its IR, NMR and mass spectra. Elementary analysis found 60.81% C (calculated 61.09), 9.73% H (calculated 9,61) and 20.20% S (calculated 20.39).

c) Human albumin is modified with 2-N-tert-butyliminothiolane obtained as described in Example I and then labelled with Tc-99m as described in Example XVI. The labelling yield is 91.2%.

EXAMPLE XIX

Preparation of 4-mercaptomethyl-2-iminothiolane and of 4-acetylthiomethyl-2-iminothiolane: use of these compounds a) A solution of 217 g 2-isopropyl-5-hydroxymethyl-1,3-dioxane in 11 of carbon tetrachloride is added dropwise to a solution of 356 g triphenylphosphine in 1 l of carbon tetrachloride, heated to 70° C. The mixture is refluxed and after approx. 1 hour cooled down (ice-bath), filtrated and evaporated. The residue is repeatedly treated with diethylether and filtered. After evaporating the filtrate the residue is purified by distillation. The desired 2-isopropyl-5-chloromethyl-1,3-dioxane is obtained as a colorless liquid; b.p. 84°–94° C. mm Hg; cis-trans mixture; identification by NMR.

b) A mixture of 183 g 2-isopropyl-5-chloromethyl-1,3-dioxane, 25 g of water and 5 ml of conc. hydrochloric acid is refluxed overnight. After cooling and adding diethylether, 2-chloromethyl-l,3-propanediol is isolated by extraction with water. The aqueous layers are washed with diethylether and evaporated. The residue is dissolved in acetone, dried and evaporated. The product is obtained as a colorless liquid and identified by IR and NMR.

c) To 16.2 g of powdered NaCN in 100 ml of DMSO, heated to 140° C., is added 32.8 g of the above 2-chloromethyl-1,3-propanediol, dissolved in an equal volume of DMSO. The temperature rises to approx. 160°–170° C. during the addition. After cooling down to room temperature the mixture is diluted with 2–3 times the volume of acetone. The mixture is filtered over Na$_2$SO$_4$. The filtrate is evaporated by distilling DMSO therefrom in vacuo. The desired 2-cyanomethyl-1,3-propanediol is obtained by extracting the residue with 2 portions of 400 ml acetone. After drying and evaporating the solvent, the product is obtained in a yield of 23 g: b.p. 200° C./0.005 mm Hg. Identification by IR and NMR.

d) A solution of 60 g tosylchloride in 400 ml benzene is added to a stirred and cooled mixture of 17.5 g 2-cyanomethyl1,3 propanediol, 1.3 g triethylbenzylammonium chloride and 150 ml 30% (w/w) aqueous NaOH solution. This mixture is stirred overnight. The organic and aqueous layers are separated and the aqueous layer is washed with diethylether. The combined organic phase is washed with water until neutral, dried and evaporated. 2-Cyanomethyl-1,3-bis(tosyloxy)propane is obtained in a obtained in a yield of 62 g; liquid. Identification by means of IR, NMR and mass spectra.

e) A solution of 62 g of 2-cyanomethyl-1,3-bis(tosyloxy)propane in 250 ml DMSO is added dropwise to a stirred solution of 36 g potassium thioacetate in 200 ml of DMSO. After stirring for one hour and adding additional DMSO, the mixture is poured into ice/water. Extraction with diethylether yields a colored organic layer which is washed successively with aqueous NaOH, water and saturated NaCl solution until neutral. Drying and evaporating yields the desired 2-cyanomethyl-1,3-bis(acetylthio)propane as a slightly yellow liquid; b.p. 146°–150° C./0.50.1 mm Hg; yield 20 g. Identification by IR and NMR.

f) A solution of 20 g of HCl in methanol (2.1 mmol HCl per 1 g of solution) is added to a solution of 6.3 g 2-cyanomethyl-1,3-bis(acetylthio)propane in 15 ml of dry methanol. After 1.5 hr reflux the solution is evaporated. The title compound, viz. 4-mercaptomethyl-2-iminothiolane, as its HCl-salt is obtained in a yield of 4.9 g. The liquid compound is identified by IR, H NMR and $^{13}$C NMR. The $^{13}$C NMR (75.4 MHz) data are: δ:26.9 (CH$_2$SH), 41.9

(CH$_2$S), 45.0 (CH$_2$), 46.1 (CH) and 205.9 (C=N). The HCl salt can easily be converted to the free iminothiolane compound by treating with a base.

g) Gaseous HCl is passed during 0.5 hour through a solution of 3 g of 2-cyanomethyl-1,3-bis(acetylthio)propane, obtained according to Example XIX e), and 1.8 g of methanol in 30 ml tetrahydrofurane; temperature 40°–55° C. The solution is evaporated; diethylether is added to the residue. The precipitate formed is aspirated off, washed with diethylether and dried. The second title compound, viz. 4-acetylthiomethyl-2-iminothiolane is obtained as its HCl sale in a yield of 600 rag; m.p. 186°–188° C. (decomp.). Identification by $^1$H NMR and $^{13}$C NMR. The compound can equally be converted to the free base.

h) Human albumin is modified With the above compounds, viz. 4-mercaptomethyl-2-iminothiolane and 4-acetylthiomethyl-2-iminothiolane, as described in Example I, and then labelled with Tc-99m as described in Example XVI. The labelling yields are 82.8 and 100% respectively.

EXAMPLE XX

Fc fragment modification with 2-iminothiolane and labelling with Tc-99m tartrate The starting material is 1 ml Fc fragment in a concentration of 10 mg/ml in 0.06M triethanolamine HCl, pH 8.0. To this solution 5/ul of 0.18M 2-iminothiolane in 1M triethanolamine HCl, pH 8.0, are added. After incubation at room temperature for 1 hour, the mixture is liberated from unreacted 2-iminothiolane by gel chromatography (Sephadex G25). 0.5 ml of Tc-99m tartrate (=10 mCi) are added and incubation at room temperature is carried out for 0.5 hour. The labelling yield is 91.5% by gel chromatography analysis.

EXAMPLE XXI

F(ab')$_2$ fragment modification with 2-iminothiolane and labelling with Tc-99m tartrate The starting material is 1 ml F(ab')$_2$ fragment in a concentration of 10 mg/ml in 0.06M triethanolamine HCl, pH 8.0. To this solution 5/ul of 0.18M 2-iminothiolane in 1M of triethanolamine HCl, pH 8.0 are added. After incubation at room temperature for 1 hour, the mixture is liberated from unreacted 2-iminothiolane by gel chromatography ( Sephadex G25 ). 0.5 ml of Tc-99m tartrate (=10 mCi) are added, and incubation at room temperature is carried out for 0.5 hour. The labelling yield is 92.8% by gel chromatography analysis.

We claim:

1. A bifunctional chelating agent capable of reaction with a proteinaceous material to form a protein conjugate and with a radionuclide to form a radionuclide complex, wherein it is 2-N-tert-butyliminothiolane.

2. A bifunctional chelating agent capable of reaction with a proteinaceous material to form a protein conjugate and with a radionuclide to form a radionuclide complex, wherein it is 4-mercaptomethyl-2-iminothiolane.

3. A bifunctional chelating agent capable of reaction with a proteinaceous material to form a protein conjugate and with a radionuclide to form a radionuclide complex, wherein it is 4-acetylthiomethyl-2-iminothiolane.

* * * * *